United States Patent [19]
Merrifield et al.

[11] Patent Number: 6,077,536
[45] Date of Patent: *Jun. 20, 2000

[54] PHARMACEUTICAL FORMULATION

[75] Inventors: David Roy Merrifield; Paul Laurence Carter, both of Worthing; David George Doughty, Epsom, all of United Kingdom

[73] Assignee: Beecham Group plc, Brentford, United Kingdom

[ * ] Notice: This patent is subject to a terminal disclaimer.

[21] Appl. No.: 09/136,444

[22] Filed: Aug. 19, 1998

Related U.S. Application Data

[62] Division of application No. 08/328,313, Oct. 24, 1994, Pat. No. 5,814,337, which is a continuation of application No. 07/934,757, Oct. 7, 1992, abandoned.

[30] Foreign Application Priority Data

Apr. 7, 1990 [GB] United Kingdom .................. 9007945

[51] Int. Cl.$^7$ ...................................... A61K 9/46
[52] U.S. Cl. .......................... 424/466; 424/489; 514/210; 514/962
[58] Field of Search .................... 424/466, 489; 514/210, 962

[56] References Cited

U.S. PATENT DOCUMENTS

| | | |
|---|---|---|
| 3,105,792 | 10/1963 | White . |
| 3,495,001 | 2/1970 | Leonards . |
| 4,110,165 | 8/1978 | Cole et al. . |
| 4,301,149 | 11/1981 | Crowley . |
| 5,180,590 | 1/1993 | Carcano . |
| 5,225,197 | 7/1993 | Bolt et al. . |
| 5,814,337 | 9/1998 | Merrifield et al. ...................... 424/466 |

FOREIGN PATENT DOCUMENTS

| | | |
|---|---|---|
| 710859 | 8/1968 | Belgium . |
| 0080862 | 6/1983 | European Pat. Off. . |
| 27 50 207 | 11/1978 | Germany . |
| 79019 | 6/1982 | Romania . |
| 1221038 | 2/1971 | United Kingdom . |
| 1276839 | 6/1972 | United Kingdom . |
| 1300998 | 12/1972 | United Kingdom . |
| WO 88/09173 | 12/1988 | WIPO . |

OTHER PUBLICATIONS

Tsuji, et a., Journal of Pharmaceutical Sciences, vol. 67 (8) Aug. 1978, pp. 1059–1066.

*Primary Examiner*—Jyothsna Venkat
*Attorney, Agent, or Firm*—Dara L. Dinner; Stephen Venetianer; Charles M. Kinzig

[57] ABSTRACT

A pharmaceutical formulation comprising an amoxycillin hydrate and an effervescent couple, for example citric acid plus sodium bicarbonate or sodium glycine carbonate, or tartaric acid or malic acid plus sodium carbonate. Potassium equivalents of these sodium salts may be used. The formulations may be free flowing powders or granules, or tablets.

21 Claims, No Drawings

PHARMACEUTICAL FORMULATION

This is a divisional of application Ser. No. 08/328,313 filed Oct. 24, 1994 U.S. Pat. No. 5,814,337 which is a continuation of application Ser. No. 07/934,757 filed Oct. 7, 1992 (abandoned).

The present invention relates to pharmaceutical compositions for oral administration in the treatment of bacterial infections.

In some clinical situations, to improve patient compliance, it is desirable to administer medicaments orally in liquid form as suspensions or solutions.

EP-A-0080862 (Beecham) discloses water-dispersible compositions of amoxycillin trihydrate, in which the amoxycillin trihydrate and other ingredients are formulated with a non-hygroscopic water-soluble binder.

Solutions are favoured over suspensions for oral administration, since drugs in solution are more rapidly absorbed. Solutions are also often more acceptable to patients, in terms of patatability. It has been proposed to prepare dry effervescent formulations of medicaments in which, on addition to water, a medicament is dispersed in the water by the effervescing action and dissolves either as a result of the agitation or by interaction with components of the formulation. For example, GB-A-1287475 (Aspro-Nicholas) describes an effervescent formulation of aspirin. In order to obtain effective contact of the aspirin with the solubilising compounds during effervescence, the aspirin particles are pre-coated with a special readily wettable coating.

Effervescent formulations of antibiotics are disclosed in GB-A-1300998 (Biochemie). In this disclosure it is considered essential that the antibiotic is in the form of a water-soluble salt in the dry formulation. For amoxycillin this would be disadvantageous because the water-soluble sodium salt is very hygroscopic and unstable when it has absorbed water.

A dispersible tablet formulation containing amoxycillin is disclosed in EP-0281200-A1 (Gist-Brocades). This formulation does not result in a clear solution of dissolved amoxycillin, but a suspension.

We have now discovered that amoxycillin that is not in salt form can be provided as an effervescent formulation in which it is solubilised on contact with water, and in particular that will produce a clear solution for oral administration.

According to the present invention there is provided a pharmaceutical formulation comprising an amoxycillin hydrate and an effervescent couple which comprises an acid component and an alkaline component, which generates carbon dioxide on contact with water, in which the alkaline component of the couple is present in excess of the stoichiometric equivalent of the acid component.

The amoxycillin hydrate is preferably amoxycillin trihydrate and may be provided in conjunction with a β-lactamase inhibitor, such as clavulanic acid or a salt thereof preferably potassium clavulanate. A suitable ratio range of amoxycillin:clavulanic acid or clavulanate salt equivalent is 12:1 to 1:1, preferably 7:1 to 1:1, 4:1 to 1:1 or 2:1 to 1:1, by weight. A suitable proportion of amoxycillin in the formulation is 10–30% by weight, e.g. 10–25%.

The effervescent couple is preferably based on citric acid and sodium bicarbonate or sodium glycine carbonate, but other solid acid/carbonate couples may be used, for example tartaric or malic acid and sodium carbonate or potassium bicarbonate or mixtures of these acid and alkaline components. The effervescent couple is provided in a sufficient amount to rapidly disperse and assist dissolution of the components of the formulation. The corresponding potassium salts of the alkaline component may be used together with the sodium salts (or as a substitute) to avoid excessive levels of sodium ions. This may be necessary when high doses of amoxycillin are included in the composition.

The alkaline component should be present in sufficient amount to both neutralize the acid component and to solubilise the amoxycillin by formation of soluble e.g. sodium/potassium, salts. The aim is that the resulting aqueous solution should have a pH of not less than 8 to achieve solubilization of amoxycillin trihydrate. Typically the composition may contain 50–75% of an alkaline component such as sodium or potassium hydrogen carbonate or glycine carbonate, by weight. A suitable mixed alkaline component is a 3–1.5:1, for example 2.5–2:1 by weight mixture of sodium glycine carbonate:potassium bicarbonate.

Typically the composition may contain 2–25%, e.g. 5–20%, e.g. 5–17.5%, by weight of an acid component such as citric acid.

The amounts of effervescent couple and excess alkaline component required to achieve rapid and complete solubilisation of a particular amoxycillin dosage can be determined by simple experiments. For doses of amoxycillin of 1 g or more, suitable ranges of molar ratios of sodium glycine carbonate:amoxycillin:potassium bicarbonate:citric acid in the formulation are 4–10:1–3:5–10:1, for example 5–8:1.5–2.5:6.5–7.5:1. Citric acid is tribasic, and suitable molar ratios of other acids may be calculated accordingly. The suitable molar ratio expressed above corresponds to a weight ratio sodium glycine carbonate 4.8–12:amoxycillin 1.9–5.7:potassium bicarbonate 2–6–5.1:citric acid 1, with a preferred weight ratio of sodium glycine carbonate:amoxycillin of at least 1.66.

Suitable ranges of molar ratios of sodium glycine carbonate:amoxycillin:citric acid are 1.5–4.5:0.2–1:1. The suitable molar ratio expressed above corresponds to a weight ratio sodium glycine carboante:amoxycillin:citric acid of 1.7–5.5:0.4–1.9:1.

For lower doses of amoxycillin, for example 500 mg, 250 mg and 125 mg the levels of sodium ions is not excessive and the inclusion of potassium bicarbonate is not necessary.

Conventional excipients, such as colourings, fillers, diluents, sweeteners and flavourings may be added to the formulations, typically in an amount up to around 10% by weight, e.g. 1–7.5%. A suitable sweetener is aspartame.

The formulations are typically in the form of free flowing powders or granules, or tablets.

Soluble tablets may contain conventional water-soluble lubricants such as sodium lauryl sulphate or sodium benzoate, typically up to around 7.5% or less. Alternatively tablets may be made using external lubrication on liquid-lubricated presses, or on double-sided presses where solid lubricant placebo compacts containing, for example, magnesium stearate are made on one side, continuously pre-lubricating the dies. The manufacturing method may be entirely conventional, e.g. formation of a granulate intermediate containing some or all of the milled components, followed by optionally blending with the other components and then pressing into tablets.

Soluble tablets are preferably conventionally packaged in protective containers such as screw cap bottles, aluminium foil sachets, plastics or metal tubes, or aluminium blister packs. Soluble powders or granules are preferably conventionally packaged in individual aluminium foil sachets, each containing a unit dose of the antibiotic. It may be appropriate to incorporate a desiccant in the packaging.

The amount of amoxycillin in a unit dose will depend on the infection to be treated and the assay of the amoxycillin. The unit-dose will be repeated according to the usual regime for amoxycillin treatments. Typically a unit dose may contain 3000, 875 or 125 mg of amoxycillin per tablet or sachet, or an intermediate dose.

The invention also provides a formulation as defined above for use in the treatment of bacterial infections in humans or animals.

The invention also provides a method of treatment of bacterial infections in humans or animals which comprises administering to the human or animal patient a formulation as defined above in an antibacterially effective amount.

The invention also provides a process for the preparation of a pharmaceutical formulation which comprises admixing an amoxycillin hydrate and an effervescent couple, the couple comprising an acid component and an alkaline component which generates carbon dioxide on contact with water, the alkaline component of the couple being present in excess of the stoichiometric equivalent of the acid component.

The invention also provides a use, of an admixture of an amoxycillin hydrate and an effervescent couple, the couple comprising an acid component and an alkaline component which generates carbon dioxide on contact with water, the alkaline component of the couple being present in excess of the stoichometric equivalent of the acid component, in the manufacture of a medicament for the treatment of bacterial infections.

The invention is illustrated by the following Examples.

EXAMPLE 1

| 3 g Dose Soluble Sachet | | |
|---|---|---|
| Ingredients | g/dose | % w/w |
| Amoxycillin trihydrate (as free acid) | 3.000 | 22.5 |
| Potassium bicarbonate | 2.800 | 21.04 |
| Sodium glycine carbonate | 6.212 | 46.7 |
| Citric acid | 0.800 | 6.01 |
| Aspartame | 0.150 | 1.13 |
| Sodium saccharin | 0.040 | 0.30 |
| Lemon juice flavour | 0.220 | 1.65 |
| Cinnamon flavour | 0.085 | 0.64 |

Reconstitution: Add the contents of each sachet to 200 mls of water and stir gently.

Manufacturing Process

The amoxycillin trihydrate was passed through an Apex 114 mill fitted with a 0.027 inch (0.686 mm) aperture screen using hammers forward at 4590 rpm.

The potassium bicarbonate, sodium glycine carbonate, aspartame, dried saccharin sodium and citric acid were passed through a 30 mesh screen and placed in a blender with the milled amoxycillin trihydrate. The mix was blended for 20 minutes at slow speed. The blend was then passed through a roller compactor, and the compact passed through an Apex 114 mill fitted with a 0.063 inch (1.6 mm) aperture screen, using knives forward at 2880 rpm, into a blender.

The flavours were screened through a 20 mesh screen into the blender, and the mix blended for 15 minutes at slow speed. The final mixture was filled into sachets at a weight calculated to deliver the required dose of amoxycillin.

EXAMPLE 2

| 1 g Dose Soluble Sachets | | |
|---|---|---|
| Ingredients | mg/sachet | (% w/w) |
| Amoxycillin Trihydrate equivalent to Amoxycillin free acid | 875.0 | 19.06 |
| Potassium Clavulanate equivalent to Clavulanic acid | 125.0 | 2.72 |
| Potassium bicarbonate | 930.0 | 20.26 |
| Citric acid (anhydrous) | 270.0 | 5.88 |
| Aspartame | 40.0 | 0.87 |
| Sodium saccharin | 10.4 | 0.23 |
| Lemon dry flavour | 73.0 | 1.59 |
| Cinnamon flavour | 28.0 | 0.61 |
| Sodium glycine carbonate | 2238.6 | 48.77 |

Manufacturing Process

The amoxycillin trihydrate was passed through an Apex 114 mill fitted with a 0.027 inch (0.686 mm) screen using hammers forward at 4,600 rpm. All other ingredients were passed though a 30 mesh screen. The reduced amoxycillin trihydrate and other ingredients were blended in a suitably sized Y-cone blender for 20 minutes. The resultant mixture was compacted on a roller compactor, and the compact was reduced to granules and classified.

EXAMPLE 3

| 3.25 g Dose Soluble Sachet | | |
|---|---|---|
| Ingredients | mg/dose | % (w/w) |
| Amoxycillin trihydrate | 3000 (as free acid) | 25.0 |
| Potassium clavulanate | 250 (as free acid) | 2.08 |
| Sodium glycine carbonate | 4968 | 41.39 |
| Potassium bicarbonate | 2504 | 20.86 |
| Citric acid anhydrous | 640 | 5.33 |
| Aspartame | 150 | 1.25 |
| Sodium saccharin | 40 | 0.33 |
| Golden syrup flavour | 150 | 1.25 |
| Banana flavour | 300 | 2.5 |

EXAMPLE 4

156.3 mg Dose Soluble Tablet

| Ingredients | mg/tablet | % (w/w) |
|---|---|---|
| Amoxycillin trihydrate | 125.00 (as free acid) | 10.43 |
| Potassium clavulanate | 31.25 (as free acid) | 2.61 |
| Sodium glycine carbonate | 625.00 | 52 |
| Citric acid anhydrous | 200.00 | 16.69 |
| Sodium benzoate | 66.90 | 5.58 |
| Aspartame | 37.50 | 3.13 |
| Golden syrup flavour | 37.50 | 3.13 |
| Banana flavour | 75.00 | 6.26 |

This tablet is compressed on 9/16 inch (14.288 mm) bevel-flat punches.

EXAMPLE 5

125 mg Dose Soluble Tablets

| Ingredients | mg/tablet | % (w/w) |
|---|---|---|
| Amoxycillin trihydrate | 125.0 (as free acid) | 18.89 |
| Sodium glycine carbonate | 406.3 | 61.39 |
| Citric acid anhydrous | 93.8 | 14.17 |
| Aspartame | 12.1 | 1.83 |
| Lemon juice flavour | 17.8 | 2.69 |
| Cinnamon flavour | 6.8 | 1.03 |

Manufacturing Process

The amoxycillin trihydrate was passed through an Apex 114 mill fitted with a 0.027 inch (0.686 mm) screen, hammers forward, at 7200 rpm into a blender. The citric acid was passed through an Apex 114 mill fitted with a 0.040 inch (1 mm) screen, hammers forward, at 7200 rpm into the blender. The other ingredients except for the flavours were passed though a 30 mesh screen into the blender. The mix was blended for 20 minutes, and the blend slugged on one side of a Manesty BB4 double-sided press fitted with ½ inch (12.5 mm) round bevelled flat tooling. A lubricating mix consisting of 3% magnesium stearate in lactose was compressed on the other side of the machine. The slugs were milled on an Apex 114 mill fitted with a 0.063 (1.6 mm) inch screen, knives forward at 2900 rpm. The flavours were passed through a 30 mesh screen and blended with the reduced slugs for 20 minutes. The blend was compressed on the double-sided press fitted with the same tooling as used to prepare the slugs, and lubricated in the same manner.

EXAMPLE 6
250 mg Dose Soluble Tablets 250 mg tablets were prepared by exactly doubling the quantities described in Example 5, and using an identical process except for replacing the ½ inch (12.5 mm) punches by ⅝ inch (15.875 mm) punches.

In the formulations of Examples 1–6 above the relative proportions of components are preferably maintained within ±10% of the stated quantities.

What is claimed is:

1. A free flowing or granular powder pharmaceutical formulation consisting of an amoxycillin hydrate and an effervescent couple, the couple comprising an acid component and an alkaline component, which generates carbon dioxide on contact with water, in which the alkaline component of the couple is present in excess of the stoichiometric equivalent of the acid component and which is in a sufficient amount to both neutralize the acid component and to solubilize the amoxycillin hydrate; a sweetener, and a flavoring agent.

2. A pharmaceutical formulation according to claim 1 in which the amoxycillin hydrate is amoxycillin trihydrate.

3. A pharmaceutical formulation according to claim 1 in which the proportion of amoxycillin hydrate is 10–30% by weight.

4. A pharmaceutical formulation according to claim 1 in which the acid component of the effervescent couple is selected from the group consisting of citric acid, tartaric acid and malic acid and mixtures thereof, and the alkaline component of the effervescent couple is selected from the group consisting of sodium bicarbonate, sodium glycine carbonate and sodium carbonate, the corresponding potassium salts, and mixtures thereof.

5. A pharmaceutical formulation according to claim 1 which when made up into aqueous solution has a pH of not less than 8.

6. A pharmaceutical formulation according to claim 1 which contains 50–75 weight % of alkaline component.

7. A pharmaceutical formulation according to claim 1 in which the alkaline component is a 3–1.5:1 by weight mixture of sodium glycine carbonate:potassium bicarbonate.

8. A pharmaceutical formulation according to claim 1 which contains 5–20 weight % of the acid component.

9. A pharmaceutical formulation according to claim 1 containing a molar ratio of sodium glycine carbonate:amoxycillin:potassiumbicarbonate:citric acid in the range 4–10:1–3:5–10:1.

10. A pharmaceutical formulation according to claim 1 containing amoxycillin between 125 and 3000 mg.

11. A pharmaceutical formulation according to claim 1 in which the alkaline component is mixture of sodium or potassium hydrogen carbonate or sodium or potassium glycine carbonate.

12. A free flowing or granular powder pharmaceutical formulation provided as a unit dose, and consisting of an amoxycillin hydrate and an effervescent couple, the couple comprising an acid component and an alkaline component, which generates carbon dioxide on contact with water, in which the alkaline component of the couple is present in excess of the stoichiometric equivalent of the acid component and which is in a sufficient amount to both neutralize the acid component and to solubilize the amoxycillin hydrate; a sweetener, and a flavoring agent.

13. A pharmaceutical formulation according to claim 12 in which the amoxycillin hydrate is amoxycillin trihydrate.

14. A pharmaceutical formulation according to claim 12 in which the proportion of amoxycillin hydrate is 10–30% by weight.

15. A pharmaceutical formulation according to claim 12 in which the acid component of the effervescent couple is selected from the group consisting of citric acid, tartaric acid and malic acid and mixtures thereof, and the alkaline component of the effervescent couple is selected from the group consisting of sodium bicarbonate, sodium glycine carbonate and sodium carbonate, the corresponding potassium salts, and mixtures thereof.

16. A pharmaceutical formulation according to claim 12 which when made up into aqueous solution has a pH of not less than 8.

17. A pharmaceutical formulation according to claim 12 which contains 50–75 weight % of alkaline component.

18. A pharmaceutical formulation according to claim 17 in which the alkaline component is a 3–1.5:1 by weight mixture of sodium glycine carbonate: potassium bicarbonate.

19. A pharmaceutical formulation according to claim 1 which contains 5–20 weight % of the acid component.

20. A pharmaceutical formulation according to claim 13 containing a molar ratio of sodium glycine carbonate:amoxycillin:potassium bicarbonate:citric acid in the range 4–10:1–3:5–10:1.

21. A pharmaceutical formulation according to claim 13 containing a unit dose amount of amoxycillin between 125 and 3000 mg.

* * * * *